US 9,295,813 B2

(12) United States Patent
Kanazawa et al.

(10) Patent No.: US 9,295,813 B2
(45) Date of Patent: Mar. 29, 2016

(54) GUIDEWIRE

(71) Applicant: ASAHI INTECC CO., LTD., Nagoya-shi, Aichi (JP)

(72) Inventors: Yuuya Kanazawa, Seto (JP); Satoru Murata, Seto (JP)

(73) Assignee: ASAHI INTECC CO., LTD., Nagoya (JP)

(*) Notice: Subject to any disclaimer, the term of this patent is extended or adjusted under 35 U.S.C. 154(b) by 244 days.

(21) Appl. No.: 14/044,414

(22) Filed: Oct. 2, 2013

(65) Prior Publication Data

US 2014/0188004 A1    Jul. 3, 2014

(30) Foreign Application Priority Data

Dec. 27, 2012  (JP) ................. 2012-284224

(51) Int. Cl.
*A61M 25/09*    (2006.01)

(52) U.S. Cl.
CPC ..... *A61M 25/09* (2013.01); *A61M 2025/09133* (2013.01); *A61M 2025/09175* (2013.01)

(58) Field of Classification Search
CPC ......... A61M 2025/09066; A61M 2025/09083; A61M 2025/09091; A61M 2025/0915; A61M 2025/09175; A61M 25/09; A61M 2025/09133
See application file for complete search history.

(56) References Cited

U.S. PATENT DOCUMENTS

| | | | |
|---|---|---|---|
| 4,763,647 A * | 8/1988 | Gambale | 600/585 |
| 4,886,067 A * | 12/1989 | Palermo | A61M 25/09033 600/434 |
| 5,772,609 A | 6/1998 | Nguyen et al. | |
| 5,833,632 A | 11/1998 | Jacobsen et al. | |
| 6,251,086 B1 | 6/2001 | Cornelius et al. | |
| 2004/0167438 A1 | 8/2004 | Sharrow | |
| 2005/0054953 A1 * | 3/2005 | Ryan et al. | 600/585 |
| 2005/0096665 A1 * | 5/2005 | Reynolds et al. | 606/108 |
| 2009/0005755 A1 | 1/2009 | Keith et al. | |
| 2009/0299332 A1 | 12/2009 | Shireman | |

FOREIGN PATENT DOCUMENTS

| | | |
|---|---|---|
| CN | 102205165 A | 10/2011 |
| CN | 102727945 A | 10/2012 |
| CN | 102743813 A | 10/2012 |
| JP | A-10-071209 | 3/1988 |
| JP | A-09-294813 | 11/1997 |
| JP | A-2002-017863 | 1/2002 |

(Continued)

OTHER PUBLICATIONS

Oct. 20, 2014 Office Action issued in Japanese Patent Application No. 2012-284224 (with English Translation).

(Continued)

*Primary Examiner* — Devin Henson
*Assistant Examiner* — David J McCrosky
(74) *Attorney, Agent, or Firm* — Oliff PLC

(57) ABSTRACT

A guidewire includes a linear portion, a curved portion that is provided distally of the linear portion, a boundary portion that is provided between the linear portion and the curved portion, a lubricant portion that is provided on a surface of the linear portion, and a low lubricant portion that is provided at least on a surface of the boundary portion disposed on a side of the guidewire opposite of a direction toward which the curved portion is curved, a lubricating ability of the low lubricant portion being lower than that of the lubricant portion.

10 Claims, 13 Drawing Sheets

(56) References Cited

FOREIGN PATENT DOCUMENTS

| JP | A-2005-185376 | 7/2005 |
| JP | A-2006-518641 | 8/2006 |
| JP | A-2008-237621 | 10/2008 |
| WO | 2004/018030 A1 | 3/2004 |
| WO | WO-2004/074174 A2 | 9/2004 |
| WO | WO 2009/146339 A1 | 12/2009 |

OTHER PUBLICATIONS

Mar. 12, 2014, Office Action issued in European Application No. 131865719.

Aug. 4, 2015 Office Action issued in Chinese Patent Application No. 201310401788.2.

* cited by examiner

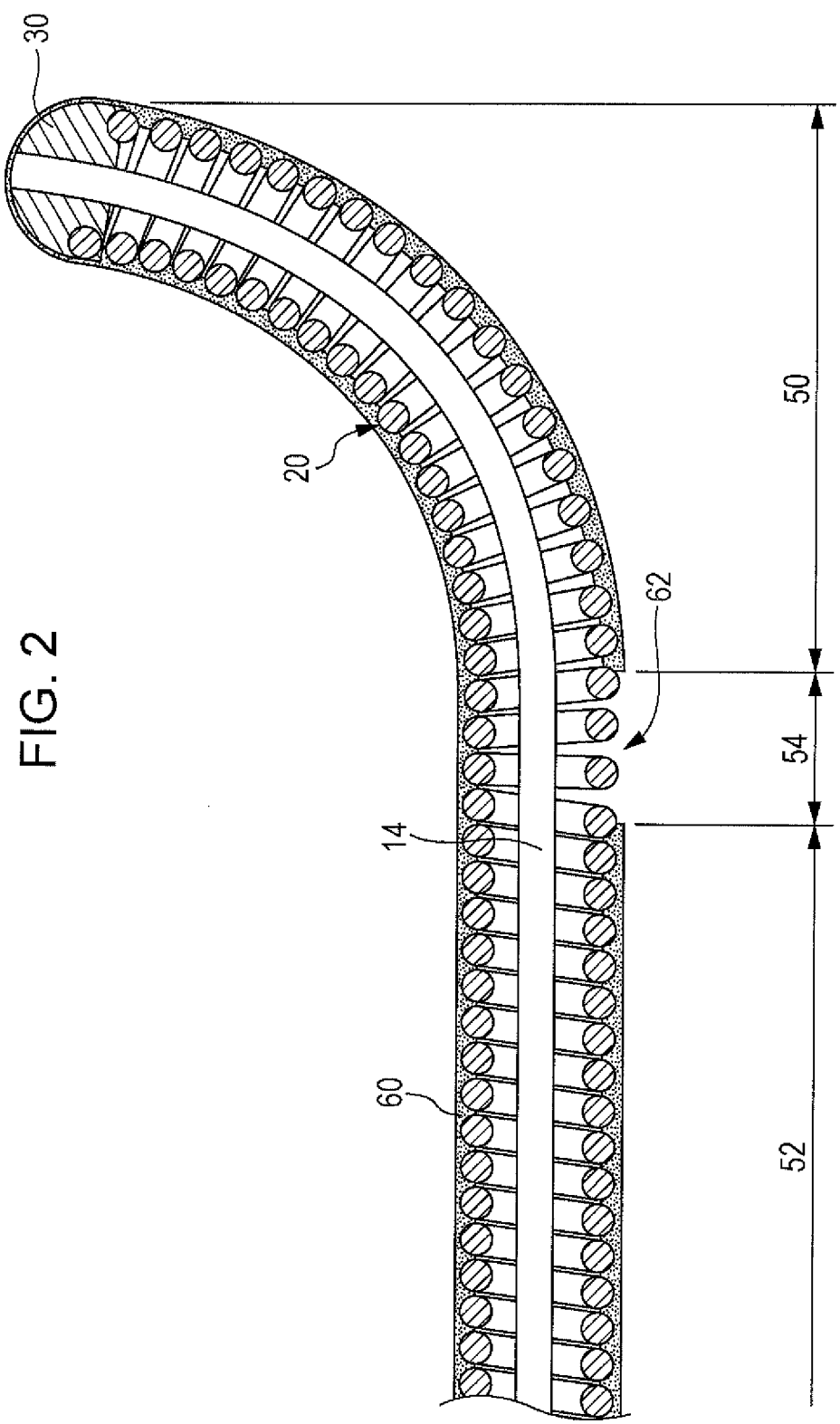

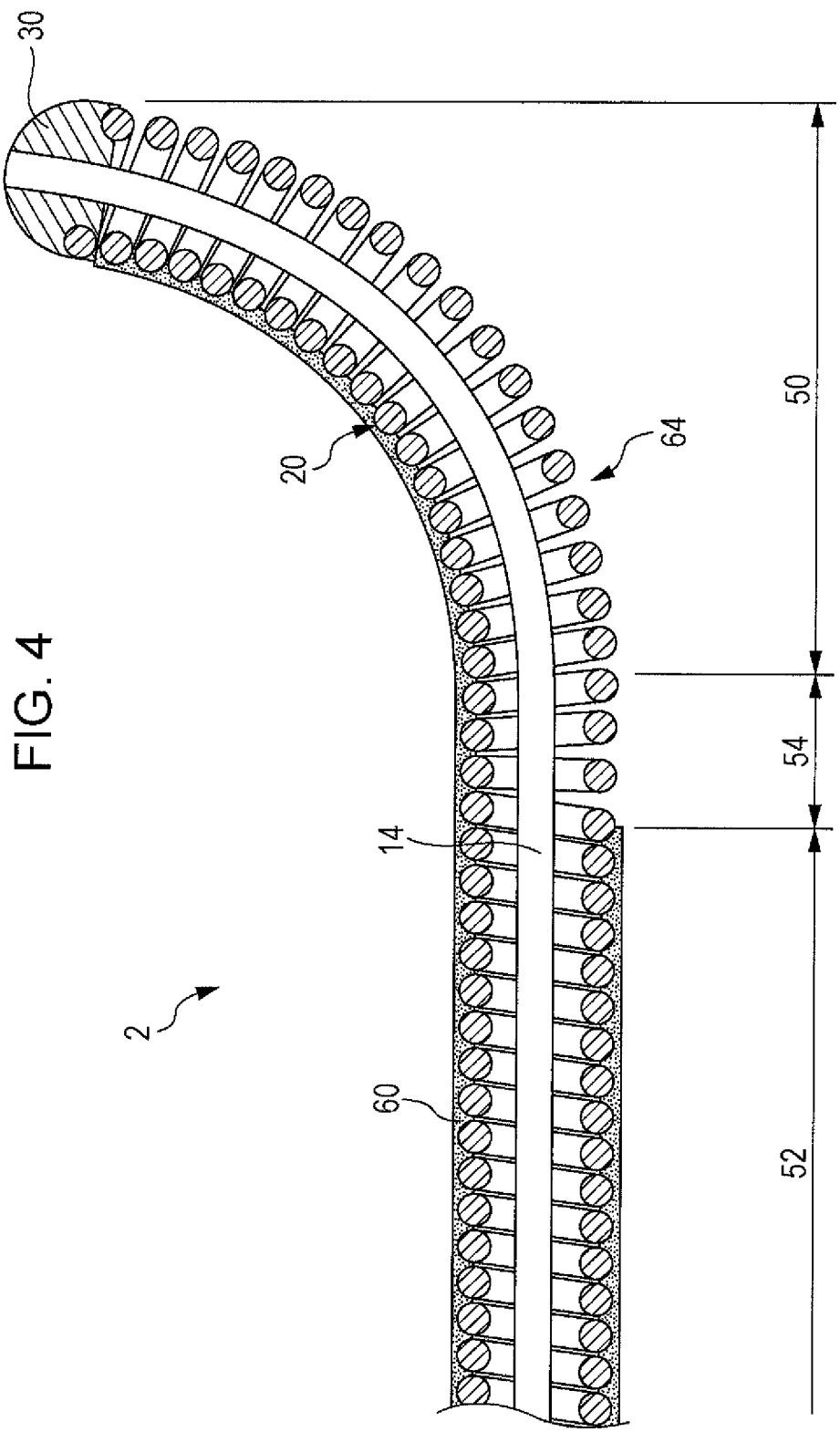

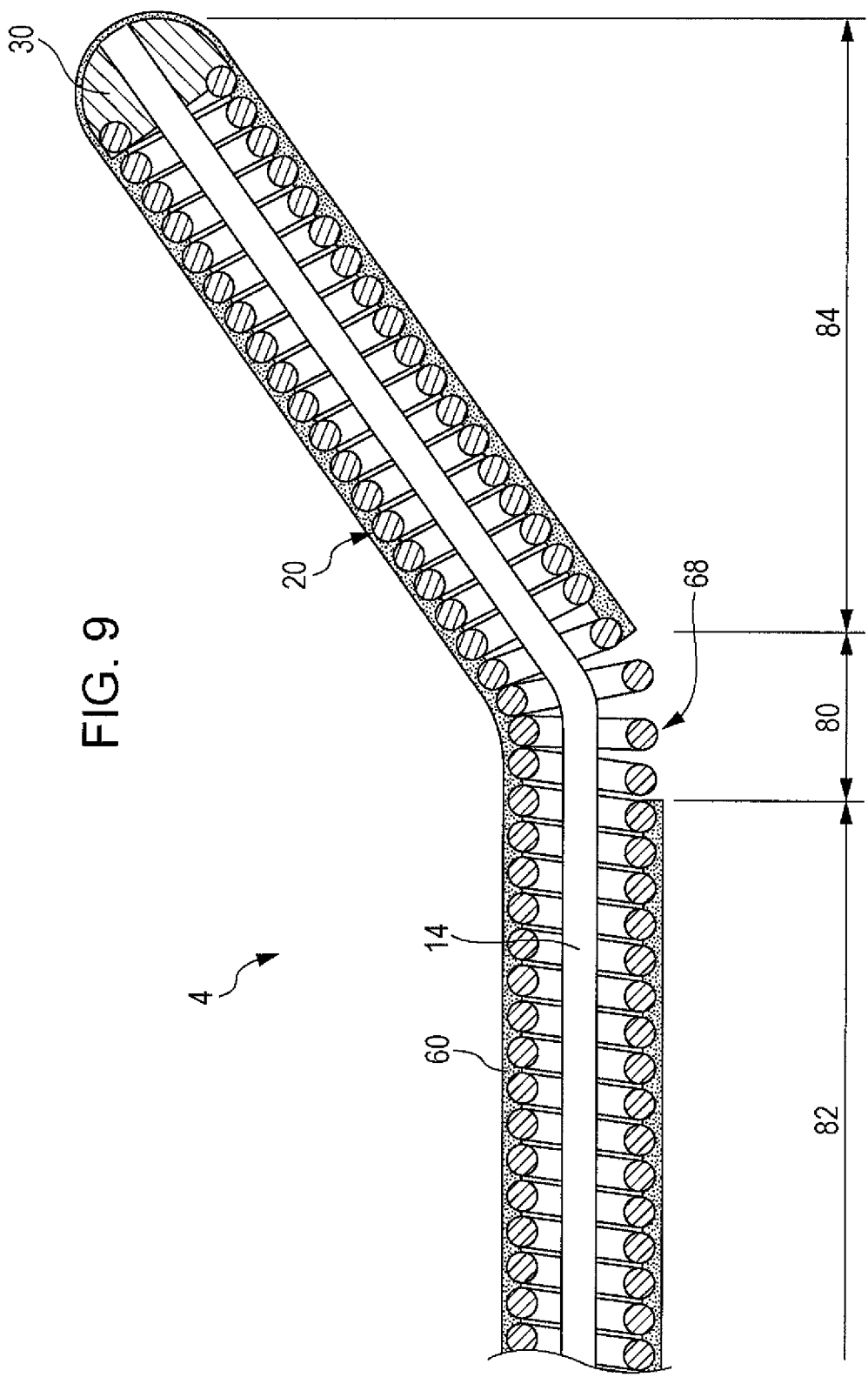

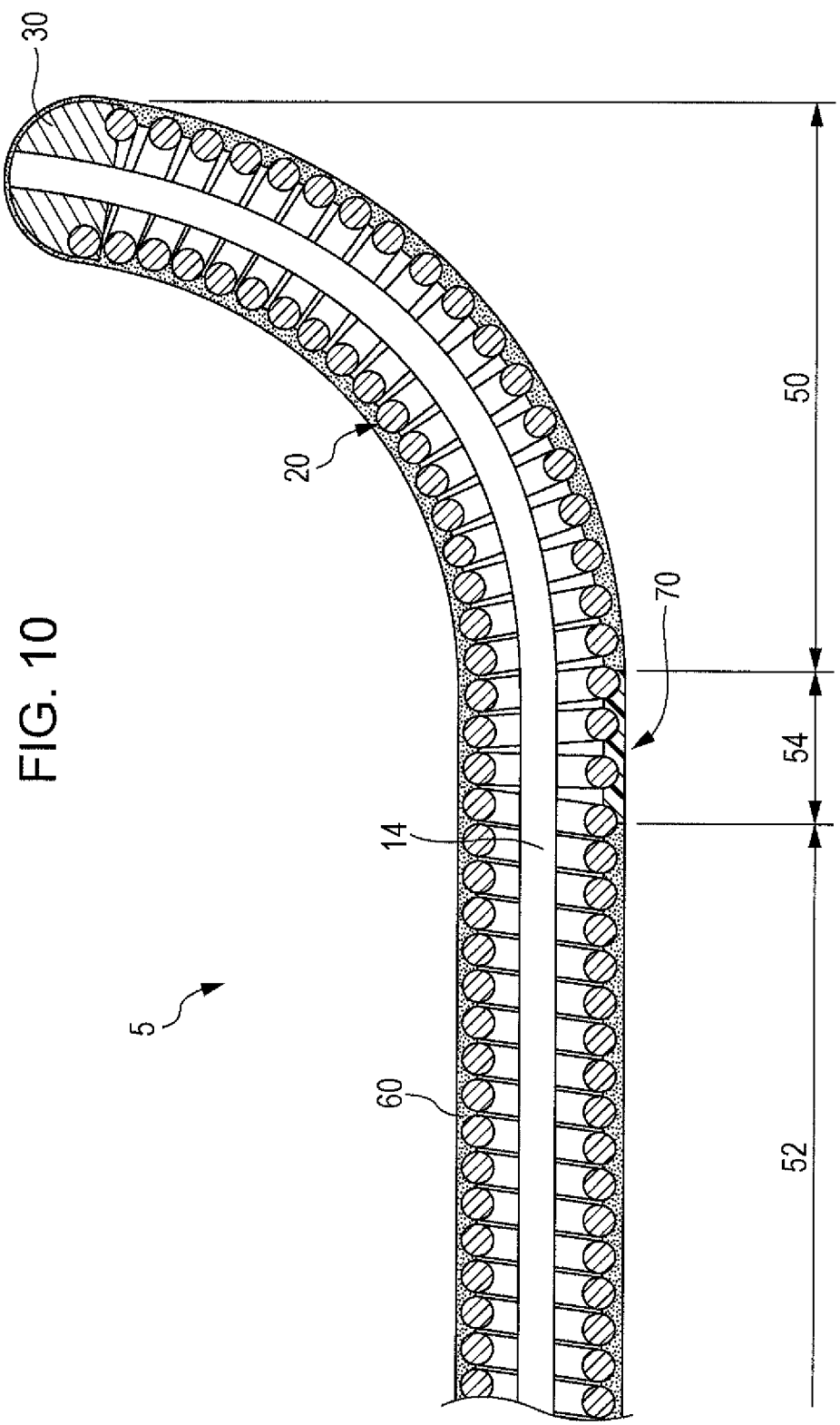

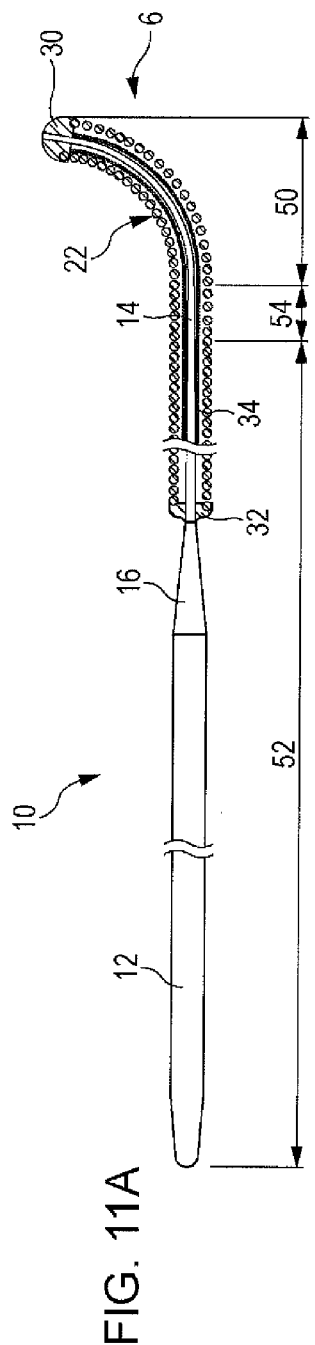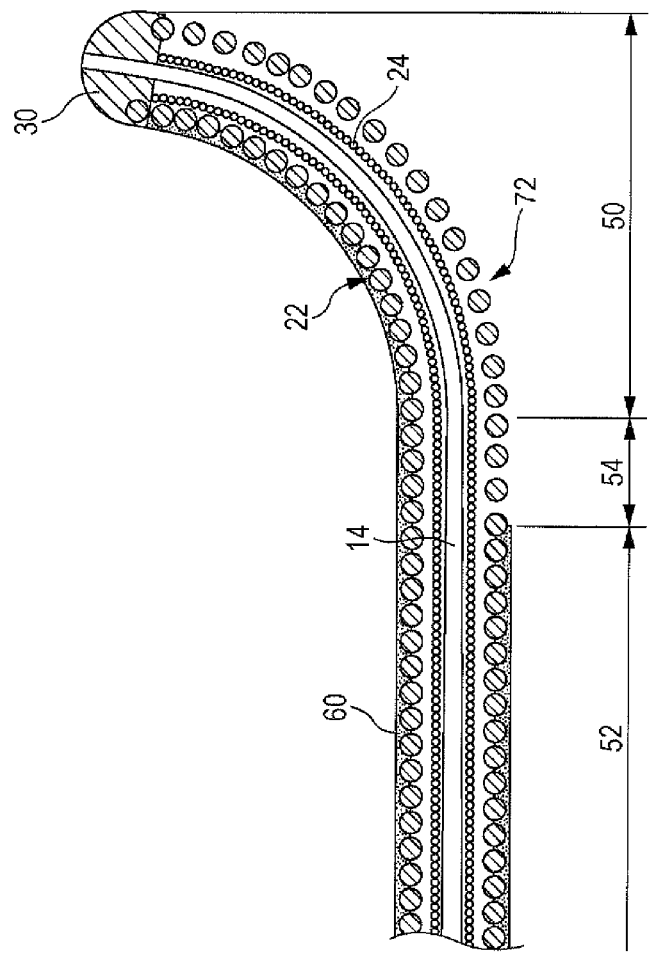
FIG. 11A
FIG. 11B

GUIDEWIRE

CROSS REFERENCE TO RELATED APPLICATION

This application claims priority to Japanese Patent Application No. 2012-284224 filed in the Japan Patent Office on Dec. 27, 2012, the entire contents of which are incorporated herein by reference.

BACKGROUND

The disclosed embodiments relate to a medical device. Specifically, the disclosed embodiments relate to a guidewire that is inserted into a lumen of, for example, a blood vessel.

A guidewire that is used when inserting a catheter into a lumen of, for example, a blood vessel, is known. When inserting a catheter, a guidewire is inserted into a lumen of, for example, a blood vessel, and is moved forward up to the vicinity of a lesion (such as an occluded part of a blood vessel). Then, the catheter is moved forward along the guidewire. In this way, with the catheter being inserted up to the vicinity of the lesion of the lumen, various treatments are performed using the catheter.

When inserting a guidewire into a lumen, a distal end of the guidewire cannot be properly oriented in the direction of a desired branch at a location where the lumen is branched. As a result, it may be difficult to move the guidewire forward into a portion of the lumen at the desired branch. Therefore, a technology that makes it easier to move the guidewire forward into a portion of the lumen at the desired branch by forming a distal end portion of the guidewire in a curved shape has been proposed (for example, Japanese Unexamined Patent Application Publication No. 9-294813).

In order to smoothly move a guidewire into a lumen, it is desirable to minimize the friction between a surface of the guidewire and an inside wall of the lumen. From such a viewpoint, a technology that covers a surface of the guidewire with, for example, a lubricant layer (such as a hydrophilic coating agent) has also been proposed (for example, Japanese Unexamined Patent Application Publication No. 2008-237621).

SUMMARY

However, when a surface of a guidewire that has a distal end portion with a curved shape is covered with a lubricant layer, it becomes difficult to fix the direction of the distal end portion of the guidewire because the surface of the guidewire slides with respect to an inside wall of a lumen. The same problem may also occur not only in a normal lumen, but also at, for example, an occluded part that is formed when cholesterol or the like is deposited on the inside wall of the lumen.

The disclosed embodiments overcome the aforementioned problems of the related art, and make it easier to fix the direction of a distal end portion of a guidewire while providing the guidewire with lubricating ability with respect to, for example, an inside wall of a lumen.

To overcome the aforementioned problem, a guidewire according to an exemplary embodiment utilizes the following structure. That is, the guidewire includes a linear portion, a curved portion that is provided distally of the linear portion, a boundary portion that is disposed between the linear portion and the curved portion, a lubricant portion that is provided on a surface of the linear portion, and a low lubricant portion that is provided at least on a surface of the boundary portion disposed on a side of the guidewire opposite of a direction toward which the curved portion is curved, a lubricating ability of the low lubricant portion being lower than the lubricating ability of the lubricant portion.

In such a guidewire, in order to reduce the friction between the guidewire and an inside wall of a lumen of, for example, a blood vessel, the lubricant portion having a high lubricating ability (that is, having a low friction resistance) is provided on a surface of the linear portion. In addition, a low lubricant portion having a lower lubricating ability (that is, having a higher friction resistance) than the lubricant portion is provided at least on a surface of the boundary portion that is provided on the side of the guidewire opposite of the direction toward which the curved portion is curved.

The lubricant portion that is provided on the surface of the linear portion may be provided, for example, over the entire length of the linear portion, or at only one portion of the linear portion (such as a distal portion of the linear portion).

When the low lubricant portion is provided on the surface of the boundary portion that is provided on the side of the guidewire opposite of the direction toward which the curved portion is curved, it is possible to suppress sliding of this portion with respect to the inside wall of the lumen by a friction force between the low lubricant portion and the inside wall of the lumen. As a result, it becomes easier to fix the direction of the distal end of the curved portion (that is, it becomes easier to orient the distal end of the curved portion), so that it is possible to reliably move the distal end of the guidewire into a portion of the lumen at a desired branch. Since the lubricant portion is provided on the surface of the linear portion of the guidewire, it is possible for the surface of the guidewire to have lubricating ability with respect to the inside wall of the lumen.

A medical guidewire according to another embodiment includes a first linear portion, a second linear portion that is provided distally of the first linear portion, a bent portion that is provided between the first linear portion and the second linear portion, a lubricant portion that is provided on a surface of the first linear portion, and a low lubricant portion that is provided at least on a surface of the bent portion disposed on a side of the guidewire opposite of a direction toward which the bent portion is bent, a lubricating ability of the low lubricant portion being lower than the lubricating ability of the lubricant portion.

With this medical guidewire, sliding of the surface of the bent portion disposed on the side of the guidewire opposite of the direction toward which the second linear portion is bent can be suppressed with respect to an inside wall of a lumen by friction force between the low lubricant portion and the inside wall of the lumen. As a result, it becomes easier to fix the direction of the distal end of the second linear portion, so that it is possible to reliably move the distal end of the guidewire into a portion of the lumen at a desired branch. In addition, the low lubricant portion is provided at the location of the guidewire as described above, the side having the low lubricant portion will become an outwardly protruding side of the guidewire. Therefore, it is possible to reliably contact the low lubricant portion against the inside wall of the lumen. As a result, it is possible to more easily orient the distal end of the guidewire.

BRIEF DESCRIPTION OF THE DRAWINGS

FIG. 2 is an enlarged view of a detailed structure of a distal end portion of the guidewire according to the first embodiment.

FIG. 4 is an enlarged view of a detailed structure of a distal end portion of a guidewire according to a second embodiment.

FIGS. 8A and 83 are each an explanatory view of a state of operation using the guidewire according to the third embodiment.

FIG. 9 is an enlarged view of a detailed structure of a distal end portion of a guidewire according to a fourth embodiment.

FIG. 10 is an enlarged view of a detailed structure of a distal end portion of a guidewire according to a fifth embodiment.

FIGS. 11A and 11B are each an explanatory view of a structure of a guidewire according to a sixth embodiment.

DETAILED DESCRIPTION OF EMBODIMENTS

Figure 1:
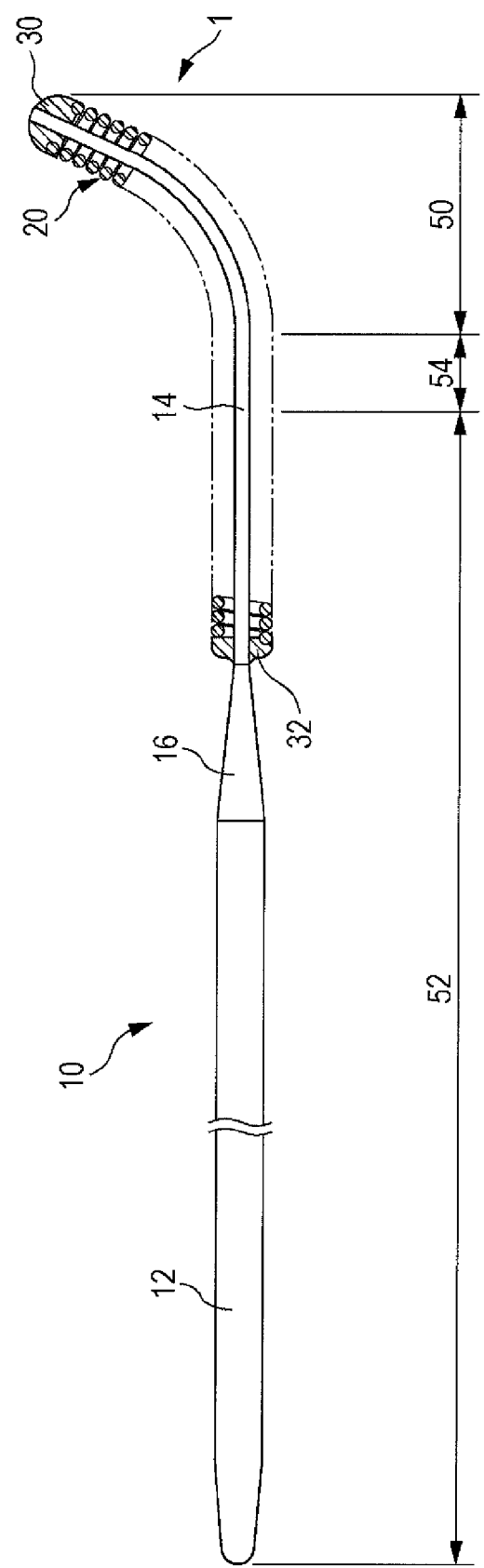
FIG. 1 is a schematic explanatory view of a structure of a guidewire according to a first embodiment.

FIG. 1 is a schematic explanatory view of a structure of a guidewire 1 according to a first embodiment. As shown in FIG. 1, the guidewire 1 according to the embodiment includes, for example, a core shaft 10 and a coil body 20 that is mounted to the core shaft 10.

The core shaft 10 includes a proximal end portion 12, a distal end portion 14 whose wire diameter is less than that of the proximal end portion 12, and a tapering portion 16 that connects the proximal end portion 12 and the distal end portion 14 to each other. The coil body 20 is secured at a distal end of the distal end portion 14 by a distal brazing portion 30, and is secured to a proximal end of the distal end portion 14 by a proximal brazing portion 32.

The shape of the core shaft 10 is not limited to the shape that is exemplified in FIG. 1. For example, the core shaft 10 may have a shape in which the diameter of the distal end portion 14 decreases from a proximal end to a distal end. Such a shape makes it possible to increase flexibility of a distal end portion of the guidewire 1. As a suitable material of the core shaft 10, for example, stainless steel (SUS) or a superelastic alloy such as an Ni—Ti alloy, is used.

The guidewire 1 according to the embodiment is gently bent at a position along the coil body 20 so that a distal end of the guidewire 1 has a curved shape. In the description below, a portion having a curved shape at the distal end of the guidewire is called a curved portion 50, a portion of the guidewire that is closer to the proximal end than the curved portion 50 is called a linear portion 52 (the straight portion of the guidewire 1), and a boundary portion between the curved portion 50 and the linear portion 52 is called a boundary portion 54.

FIG. 2 is an enlarged view of a detailed structure of the vicinity of the distal end of the guidewire 1 according to the first embodiment. As shown in FIG. 2, a surface of the guidewire 1 (more precisely, a surface of the coil body 20) is covered with a lubricant portion 60 in the form of a thin layer. Materials that are more unlikely to generate friction with respect to an outside portion than the surface of the guidewire 1 (here, the surface of the coil body 20) are used. Examples of such materials are fluorocarbon resin, silicone oil, cellulose-based high polymer materials, polyethylene oxide based high polymer materials, maleic anhydride based high polymer materials (such as maleic anhydride copolymer including methyl vinyl ether-maleic anhydride copolymer), acrylamide based high polymer materials (such as polyacrylamide, polyglycidyl methacrylate-dimethylacrylamide block copolymer), water-soluble nylon, polyvinyl alcohol, polyvinyl pyrrolidone, and hyaluronate. Although, in FIG. 2, the state in which the lubricant portion 60 is provided on the surface of the coil body 20 is exemplified, the lubricant portion 60 may also be provided on a surface of the core shaft 10 that is closer to the proximal end than the coil body 20.

In the guidewire 1 according to the embodiment, a portion that is not covered by the lubricant portion 60 (that is, a low lubricant portion 62) is provided on a surface of the boundary portion 54 disposed on a side of the guidewire opposite of a direction toward which the curved portion 50 is curved (that is, on the side having the larger radium of curvature—the side corresponding to the outer side of the curve).

The low lubricant portion 62 is formed, for example, as follows. First, the surface of the guidewire 1 is covered with the lubricant portion 60. Then, a portion of the lubricant portion 60 that is provided on the surface of the boundary portion 54 disposed on the side of the guidewire opposite of the direction toward which the curved portion 50 is curved is removed to form the low lubricant portion 62. This makes it possible to easily form the low lubricant portion 62 by only removing a portion of the lubricant portion 60.

Figure 3A:
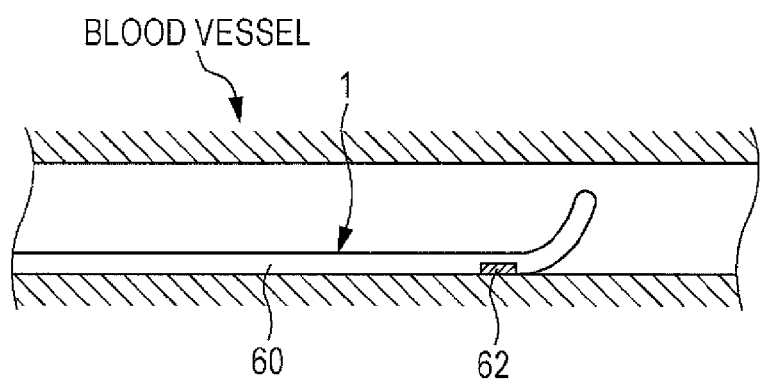
FIGS. 3A to 3C are each an explanatory view of a state of operation using the guidewire according to the first embodiment.
Figure 3B:
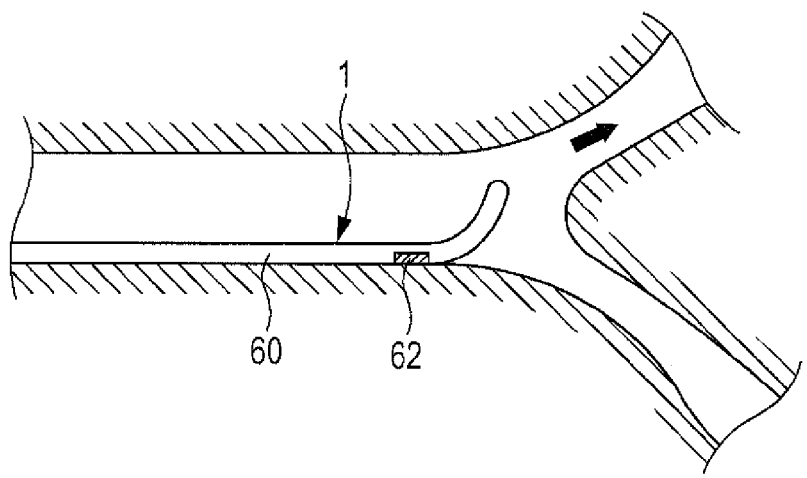
Figure 3C:
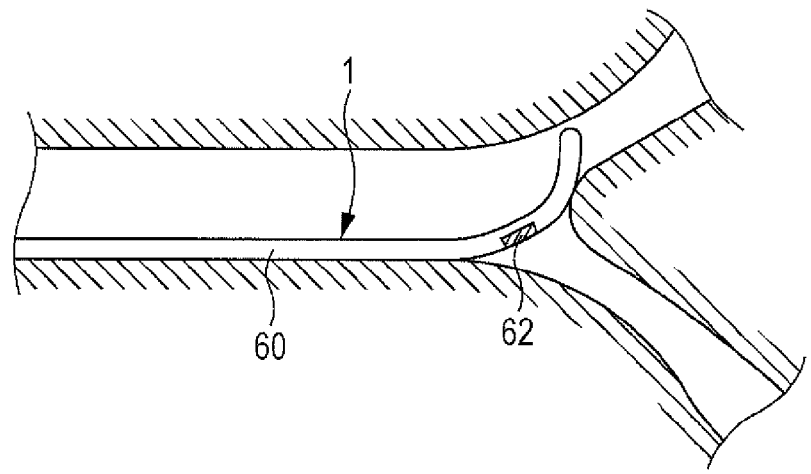

FIGS. 3A to 3C are each an explanatory view of a state of operation using the guidewire 1 according to the first embodiment. FIG. 3A shows a state in which the guidewire 1 is inserted in a blood vessel that is not branched. FIGS. 3B and 3C each show a state in which the guidewire 1 is inserted in a portion where the blood vessel is branched.

As described above, a large portion of the surface of the guidewire 1 according to the embodiment is covered by the lubricant portion 60 (see FIG. 2). Therefore, as shown in FIG. 3A, when the guidewire 1 passes through a blood vessel, the lubricant portion 60 reduces the friction between the surface of the guidewire 1 and an inside wall of the blood vessel. Consequently, the guidewire 1 can be smoothly moved through the blood vessel.

When the distal end of the guidewire 1 reaches a branched portion of the blood vessel, an operator rotates the proximal end portion 12 of the guidewire 1 while gripping the proximal end portion 12 of the guidewire 1. When this is done, as shown in FIG. 3B, the distal end of the curved portion 50 of the guidewire 1 is oriented in the direction in which the operator tries to move the guidewire 1 forward (hereunder referred to as "forward direction").

Here, with the guidewire 1 according to the first embodiment, as described above, the low lubricant portion 62 is provided on the surface of the boundary portion 54 disposed on the side of the guidewire opposite of the direction toward which the curved portion 50 is curved (see FIG. 2). Therefore, the friction force between the low lubricant portion 62 and the inside wall of the blood vessel allows the direction of the guidewire 1 to be stably maintained while the distal end of the guidewire 1 is oriented in the forward direction. Consequently, when the guidewire 1 that is in the state shown in FIG. 3B is further pushed in from the proximal end side, as shown in FIG. 3C, the operator can reliably insert the guidewire 1 into a selected blood vessel.

When the low lubricant portion 62 is provided in the vicinity of the distal end of the guidewire 1 according to the first embodiment, the low lubricant portion 62 receives resistance from the inside wall of the blood vessel (or a lesion), so that the operator can easily feel with his/her hand that the distal end of the guidewire 1 has contacted, for example, the inside wall of the blood vessel. Therefore, the operator can easily collect information regarding the vicinity of the distal end of the guidewire 1 (such as the shape of the blood vessel and the state of the legion) while the lubricating ability of the guidewire with respect to the inside wall of the blood vessel is provided by the lubricant portion 60.

The guidewire 1 according to the first embodiment is described above. Other embodiments that are related thereto are hereunder more briefly described. In the description below, structural portions that correspond to those of the above-described first embodiment are given the same reference numerals as those in the first embodiment, and are not described in detail below.

FIG. 4 is an enlarged view of a detailed structure of the vicinity of a distal end of a guidewire 2 according to a second embodiment. The illustrated guidewire 2 according to the second embodiment differs from the guidewire 1 according to the first embodiment in that the position where a low lubricant portion is provided (that is, a portion that is not covered by a lubricant portion 60) differs. That is, the low lubricant portion (low lubricant portion 64) is provided not only on a surface of a boundary portion 54 disposed on a side of the guidewire opposite of a direction toward which a curved portion 50 of the guidewire 2 is curved, but also on a surface of the curved portion 50 disposed on the side of the guidewire opposite of the direction toward which the curved portion 50 is curved.

In the second embodiment, the lubricant portion 60 is not provided on a surface of a distal brazing portion 30 (that is, the surface of the distal brazing portion 30 is defined as the low lubricant portion 64). This suppresses penetration of the distal end of the guidewire 2 through a blood vessel when the lubricating ability of the distal end of the guidewire 2 is restricted. Alternately, when the lubricating ability of a surface of the guidewire 2 takes priority, the lubricant portion 60 may also be provided on the surface of the distal brazing portion 30 (this case is not shown).

Figure 5A:
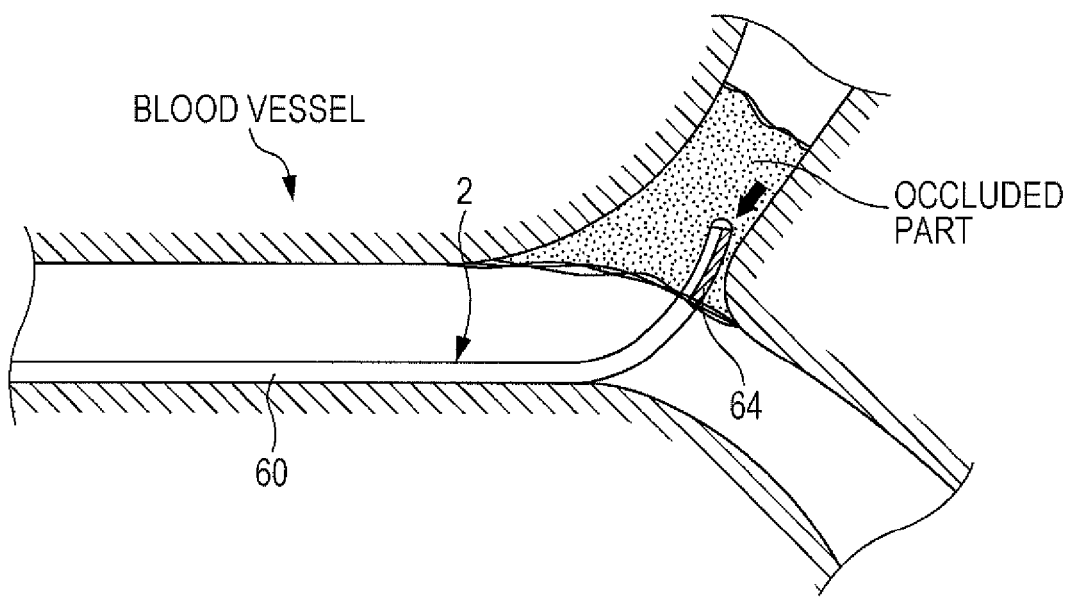
FIGS. 5A and 5B are each an explanatory view of a state of operation using the guidewire according to the second embodiment.
Figure 5B:
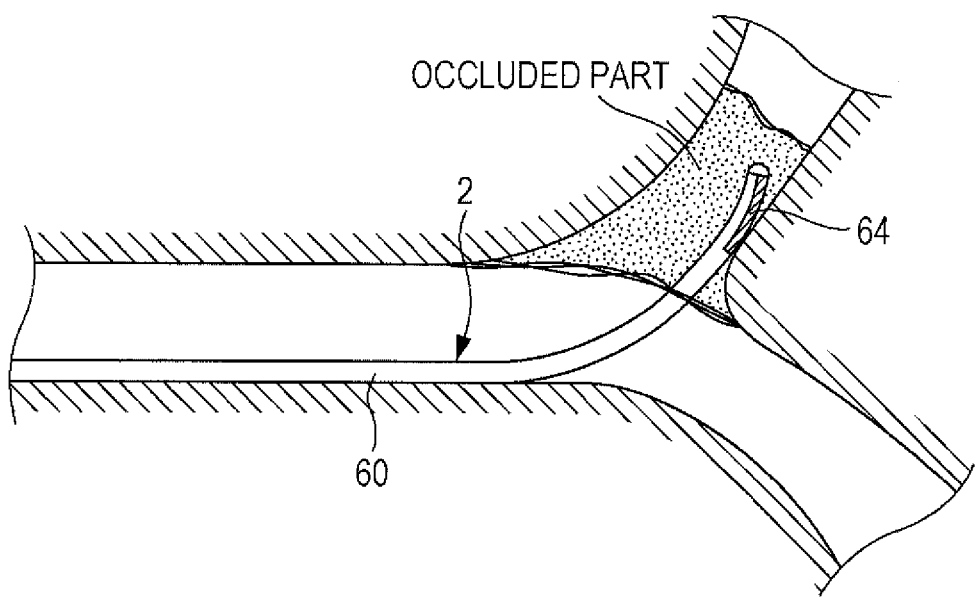

FIGS. 5A and 5B are each an explanatory view of a state of operation using the guidewire 2 according to the second embodiment. FIGS. 5A and 5B each show a state when the guidewire 2 is inserted into a portion of a blood vessel that is occluded (hereunder referred to as "occluded part") while the occluded part exists just in front of a branched portion of the blood vessel.

As shown in FIG. 5A, when an attempt is made to insert the guidewire 2 into the occluded part, the distal end of the guidewire 2 receives an opposing force (indicated by a black arrow in FIG. 5A) from the occluded part. Here, with the guidewire 2 according to the second embodiment, the surface on the side of the guidewire opposite of the direction toward which the curved portion 50 is curved is also defined as the low lubricant portion 64. Therefore, a friction force is generated between the low lubricant portion 64 and an inside wall of the blood vessel at an entrance portion of the occluded part (or the structure of the occluded part). Consequently, it is possible to prevent the guidewire 2 from falling into an illustrated lower blood vessel when the guidewire 2 receives the opposing force of the occluded part. As a result, as shown in FIG. 5B, it is possible to reliably insert the guidewire 2 into the occluded part. In addition, since the lubricant portion 60 is provided on the surface of the guidewire 2 disposed on the side of the guidewire facing a direction toward which the curved portion 50 is curved, it is possible to smoothly move the guidewire 2 into the occluded part.

Figure 6A:
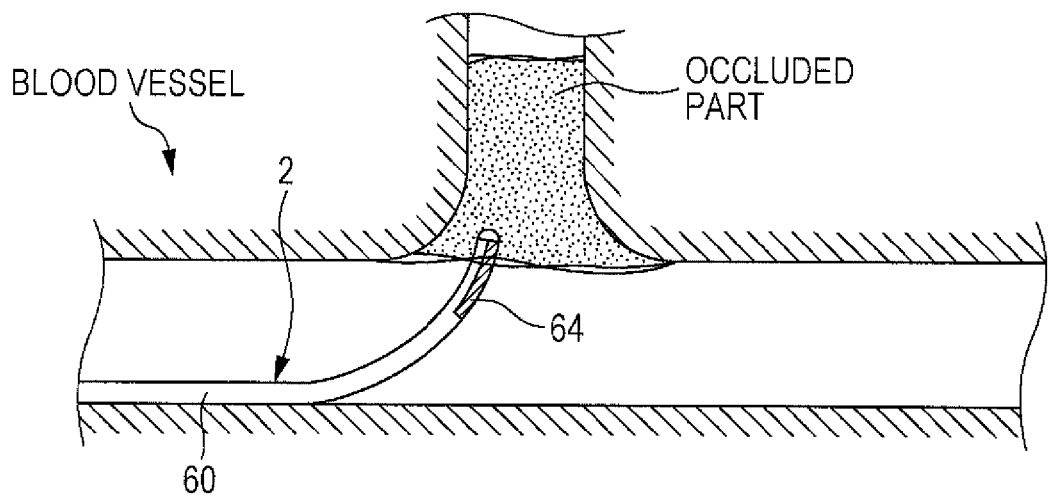
FIGS. 6A and 6B are each an explanatory view of a state of a different operation using the guidewire according to the second embodiment.
Figure 6B:
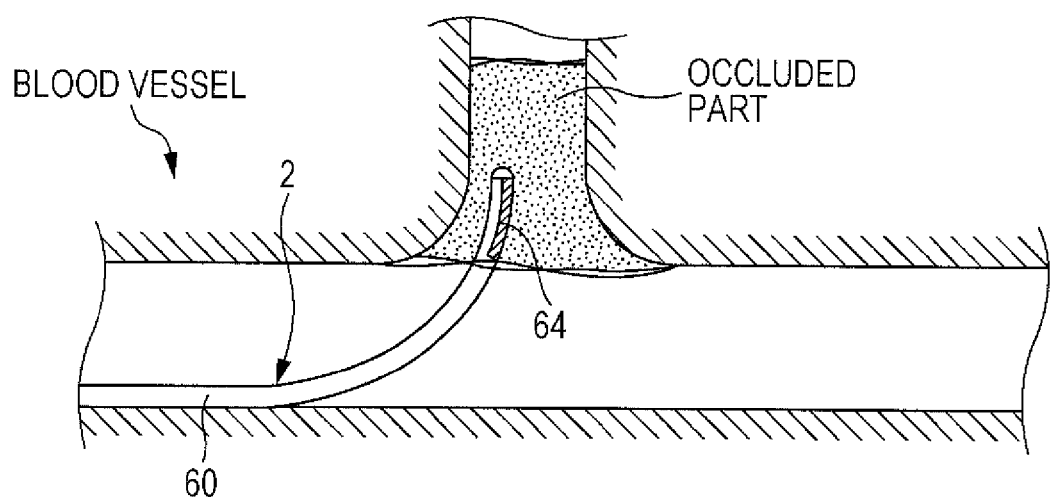

FIGS. 6A and 6B are each an explanatory view of a state of a different operation using the guidewire 2 according to the second embodiment. FIGS. 6A and 6B each show a state in which the guidewire 2 is inserted into an occluded part when a blood vessel substantially perpendicularly branches off from a linear blood vessel, and an occluded part exists right in front of the branched-off portion.

As shown in FIG. 6A, when the distal end of the guidewire 2 is inserted into an entrance portion of the occluded part, friction is generated between the low lubricant portion 64 and the structure of the occluded part. As a result, the distal end portion of the guidewire 2 is caught by the entrance portion of the occluded part. In this state, when the guidewire 2 is pushed in from a proximal-end side (illustrated left side), sliding of the distal end of the guidewire 2 in a push-in direction (illustrated right direction) is suppressed. As a result, as shown in FIG. 6B, even if the occluded part exists at the entrance portion of the blood vessel that branches off substantially perpendicularly, it is possible to reliably insert the guidewire 2 into the occluded part.

Figure 7:
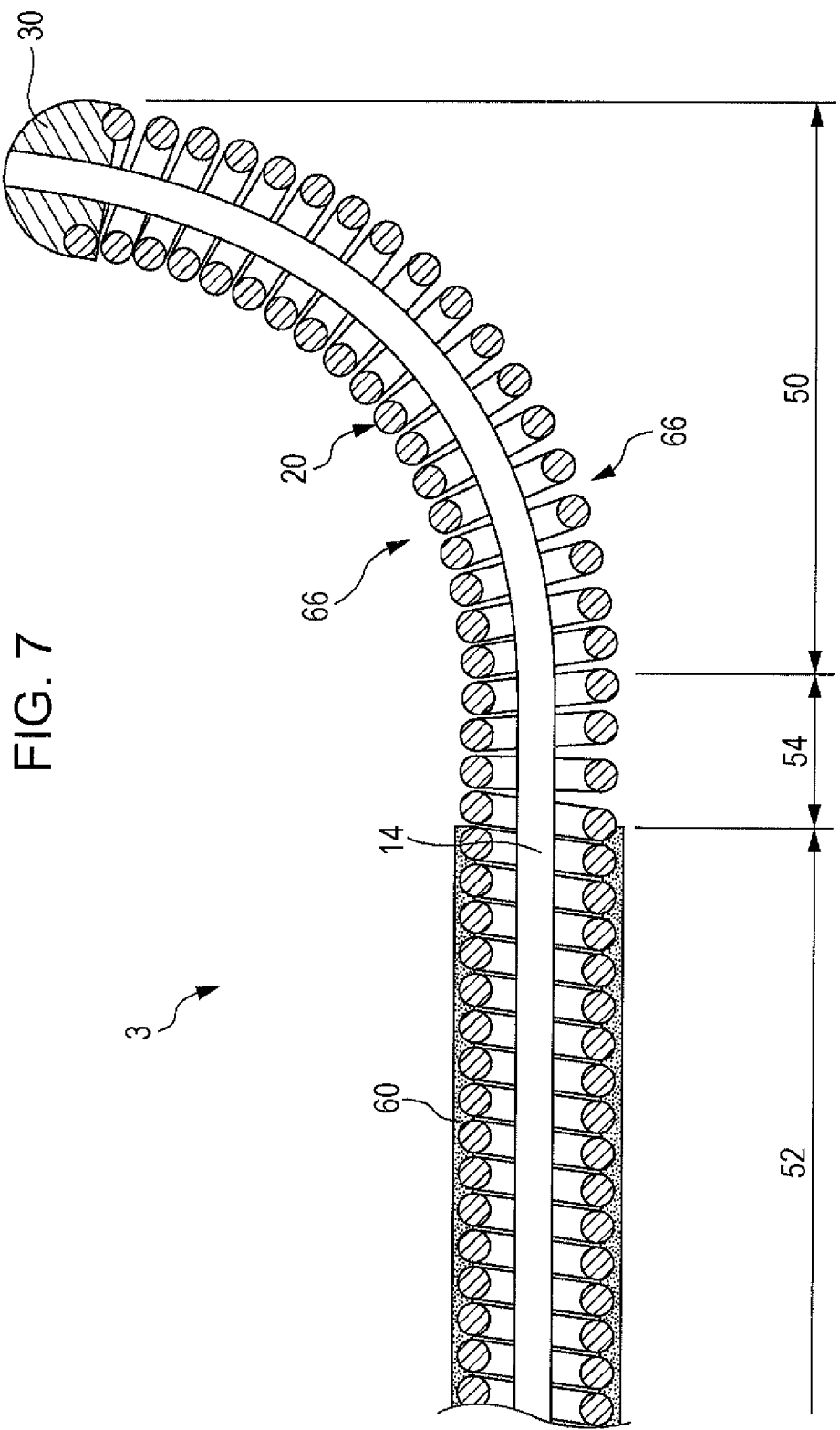
FIG. 7 is an enlarged view of a detailed structure of a distal end portion of a guidewire according to a third embodiment.

FIG. 7 is an enlarged view of a detailed structure of the vicinity of a distal end of a guidewire 3 according to a third embodiment. The illustrated guidewire 3 according to the third embodiment differs from the above-described guidewire 2 according to the second embodiment in that a low lubricant portion 66 is provided not only on a surface of a boundary portion 54 and a surface of a curved portion 50 disposed on a side of the guidewire opposite of a direction toward which the curved portion 50 is curved, but also on a surface of the boundary portion 54 and a surface of the curved portion 50 disposed on the side of the guidewire facing the direction toward which the curved portion 50 is curved.

In such a guidewire 3 according to the third embodiment, the area of the low lubricant portion 66 at the distal end of the guidewire 3 is greater than the areas of the lubricant portions in the guidewires according to the first and second embodiments. As a result, when the distal end of the guidewire 3 contacts, for example, an inside wall of a blood vessel or an occluded part, an operator gripping the proximal end portion 12 can more reliably feel with his/her hand that the distal end of the guidewire 3 has contacted, for example, an inside wall of a blood vessel or an occluded part. Therefore, the guidewire 3 according to the third embodiment can be suitably used when performing an operation (such as an operation of passing the guidewire 3 through the occluded part or an operation of inserting the guidewire 3 into a very fine blood vessel) requiring the operator to precisely feel with his/her hand that the distal end of the guidewire 3 has contacted, for example, an inside wall of a blood vessel or an occluded part.

The guidewire 3 according to the third embodiment may be suitably used in the following operations.

Figure 8A:
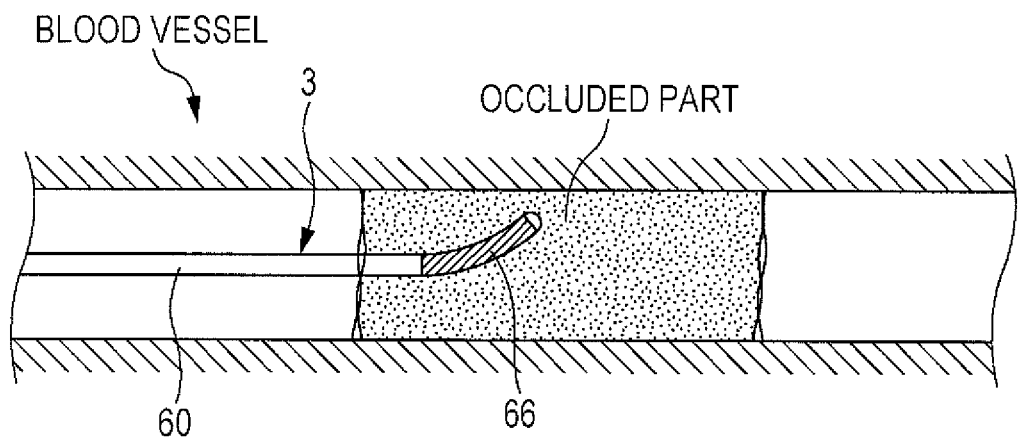
Figure 8B:
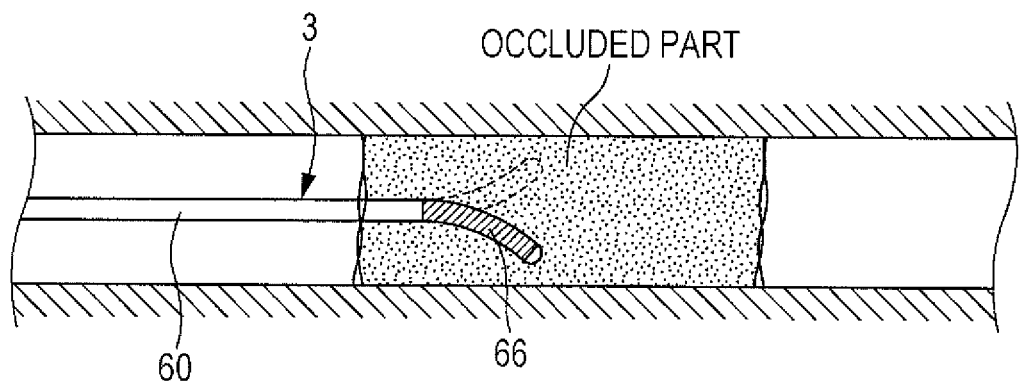

FIGS. 8A and 8B are each an explanatory view of a state of operation using the guidewire 3 according to the third embodiment. As shown in FIG. 8A, when the guidewire 3 is rotated at the proximal end while the distal end of the guidewire 3 is inserted in an occluded part of a blood vessel, the orientation of the distal end of the guidewire 3 changes. Here, when the entire surface of the guidewire is covered by a lubricant portion 60 as in existing guidewires, the surface of the guidewire slides excessively with respect to the occluded part. As a result, the distal end of the guidewire may rotate excessively by an amount that is greater than that expected by an operator. In contrast, when the entire surface of the boundary portion 54 and the entire surface of the curved portion 50 are covered by the low lubricant portion 66 as in the guidewire 3 according to the third embodiment, a friction force is sufficiently provided at the distal-end portion of the guidewire 3, so that it is possible to suppress the aforementioned excessive rotation. As a result, it is possible to easily orient the distal end of the guidewire 3 in the occluded part.

FIG. 9 is an enlarged view of a detailed structure of the vicinity of a distal end of a guidewire 4 according to a fourth embodiment. The illustrated guidewire 4 according to the fourth embodiment differs from the above-described guidewires according to the first to third embodiments in the way a distal end of the guidewire 4 is bent. That is, although each of the guidewires according to the first to third embodiments is such that its distal end is gently curved with the boundary portion 54 serving as a starting point, the guidewire 4 according to the fourth embodiment is such that its distal end is bent at a position that is separated from its distal end. In the description below, a portion where the guidewire 4 is bent is called a bent portion 80, a linear portion that is closer to a proximal end than the bent portion 80 is called a first linear portion 82, and a linear portion that is closer to a distal end than the bent portion 80 is called a second linear portion 84. In the guidewire 4 according to the fourth embodiment, a bent portion only needs to be provided between the two linear portions (that is, the first linear portion 82 and the second linear portion 84). Therefore, the bent portion 80 need not be bent at a steep angle as it is in FIG. 9. The bent portion 80 may be gently curved.

A low lubricant portion 68 is provided on a surface of the bent portion 80 disposed on a side of the guidewire opposite of a direction toward which the guidewire 4 is bent.

Even here, as with the guidewires according to the first to third embodiments, it is possible to stably maintain the direction of the distal end of the guidewire 4 by a friction force that is generated between the low lubricant portion 68 and an inside wall of a blood vessel. In addition, when this portion is provided with the low lubricant portion 68, the side having the low lubricant portion 68 is oriented to be an outwardly protruding side of the guidewire (that is, it is located on the side having the larger radius of curvature). Therefore, it is possible to reliably contact the low lubricant portion 68 and the inside wall of the blood vessel. As a result, it is possible to more easily orient the distal end of the guidewire 4. Further, in the guidewire 4 according to the fourth embodiment, by bending the coil body 20 at the bent portion 80, it is possible for the pitch in the coil body 20 at the low lubricant portion 68 to be greater than the pitches in the coil bodies 20 at the low lubricant portions of the guidewires according to the above-described first to third embodiments. Accordingly, since the surface of the guidewire 4 at the low lubricant portion 68 is very rough, it is possible to provide a sufficient friction force between the low lubricant portion 68 and the inside wall of the blood vessel.

FIG. 9 exemplifies a case in which the low lubricant portion 68 is provided on the surface of the bent portion 80 disposed on the side of the guidewire opposite of the direction toward which the guidewire 4 is bent. As in the case described above with reference to FIG. 4, the low lubricant portion 68 may be provided on the surface of the second linear portion 84 and on the surface of the bent portion 80 disposed on the side of the guidewire opposite of the direction toward which the guidewire 4 is bent (this case is not shown). This makes it possible to achieve the advantageous effects of both the second embodiment and the fourth embodiment. In addition, as in the case described above with reference to FIG. 7, the low lubricant portion 68 may be provided not only on the surface of the second linear portion 84 and the surface of the bent portion 80 disposed on the side of the guidewire opposite of the direction toward which the guidewire 4 is bent, but also on a surface of the second linear portion 84 and a surface of the bent portion 80 disposed on the side of the guidewire facing the direction toward which the guidewire 3 is bent (this case is not shown). This makes it possible to achieve the advantageous effects of both the third embodiment and the fourth embodiment.

FIG. 10 is an enlarged view of a detailed structure of the vicinity of a distal end of a guidewire 5 according to a fifth embodiment. The illustrated guidewire 5 according to the fifth embodiment differs from the other guidewires according to the first to fourth embodiments in the method of forming a low lubricant portion. That is, although, in each of the above-described guidewires according to the first to fourth embodiments, the low lubricant portion is formed by removing a portion of the lubricant portion 60, in the fifth embodiment, a portion of the guidewire 5 where the lubricant portion 60 has been removed is covered with a material (such as a resin material) having a lubricating ability that is lower than that of the lubricant portion 60, so that a low lubricant portion 70 is formed.

FIG. 10 exemplifies a form in which the guidewire 1 according to the first embodiment shown in FIG. 2 is provided with a covering having low lubricating ability at a portion thereof where a portion of the lubricant portion 60 has been removed. However, the fifth embodiment is not limited to the form exemplified in FIG. 10. The guidewire 5 according to the fifth embodiment may have, for example, a form in which the guidewire 2 according to the second embodiment shown in FIG. 4 is covered with the low lubricant portion 70 at a portion thereof where the lubricant portion 60 has been removed, a form in which the guidewire 3 according to the third embodiment shown in FIG. 7 is covered with the low lubricant portion 70 at a portion thereof where the lubricant portion 60 has been removed, or a form in which the guidewire 4 according to the fourth embodiment shown in FIG. 9 is covered with the low lubricant portion 70 at a portion thereof where the lubricant portion 60 has been removed.

Even in these cases, as with the guidewires according to the above-described first to fourth embodiments, it is possible to stably maintain the direction of the distal end of the guidewire 5 by a friction force that is generated between the low lubricant portion 70 and an inside wall of a blood vessel. In addition, when the low lubricant portion 70 is provided in this way, it is possible to change the friction force at the low lubricant portion 70 by the type of material used for the low lubricant portion 70. As a result, it is possible to set the friction force at the low lubricant portion 70 to a desired value without being influenced by the friction force on the surface of the guidewire 5 (here, the surface of the coil body 20).

FIGS. 11A and 11B are each an explanatory view of a structure of a guidewire 6 according to a sixth embodiment. FIG. 11A shows a general structure of the guidewire 6 according to the sixth embodiment. FIG. 11B shows a detailed structure of the vicinity of a distal end of the guidewire 6 according to the sixth embodiment.

AS shown in FIG. 11A, the guidewire 6 according to the sixth embodiment differs from the guide wires according to the above-described first to fifth embodiments in that a coil body structure that is provided at a distal end portion 14 of a core shaft 10 has a double structure. In the description below, a coil body at the outer side is called an outer coil body 22, and a coil body at the inner side is called an inner coil body 24. The inner coil body 24 is secured to a distal end side of the distal end portion 14 by a distal brazing portion 30, and is secured inwardly of the distal end portion 14 by an intermediate brazing portion 34.

The inner coil body 24 is, for example, a circular cylindrical body in which a single strand is spirally wound or a circular cylindrical body in which a plurality of strands are twisted together. The inner coil body 24 may be flexible or elastic.

The guidewire 6 according to the sixth embodiment is assembled as follows. First, the linear outer coil body 22, a linear core shaft 10, and the curved inner coil body 24 are provided. Then, the distal end of the core shaft 10 is inserted into and mounted to the curved inner coil body 24. Lastly, the distal end of the core shaft 10 to which the inner coil body 24 is mounted is inserted into and mounted to the linear outer coil body 22. As shown in FIG. 11B, the guidewire 6 that has been assembled in this way is formed such that the curvature of the inner coil body 24 is greater than the curvature of the outer coil body 22. This means that the outer coil body 22 is curved by a force (restoring force) that causes the inner coil body 24 to be restored to its original shape, as a result of which, as shown in FIG. 11B, the shape (curved shape) of the distal end of the guidewire 6 is maintained.

In this way, the restoring force of the inner coil body 24 acts upon the outer coil body 22 of the guidewire 6 according to the sixth embodiment at all times. Therefore, compared to guidewires formed into a similar shape by merely causing the distal end of the coil body 20 to be curved, the guidewire 6 is easily bent in the direction in which the guidewire 6 is curved when the guidewire 6 receives resistance from the distal end side of the guidewire 6.

In addition, as with the above-described guidewire 2 according to the second embodiment, the guidewire 6 includes a lubricant portion 60, provided on a surface of the outer coil body 22, and a low lubricant portion 72, provided a surface of a curved portion 50 and a surface of a boundary portion 54 disposed on a side of the guidewire opposite of a direction toward which the curved portion 50 is curved.

Figure 12A:
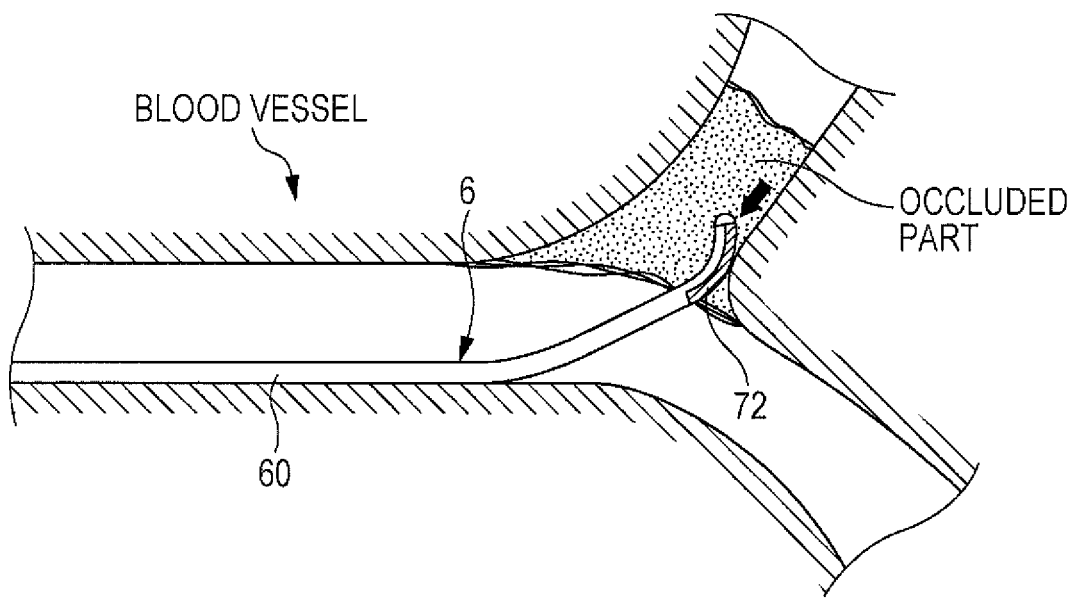
FIGS. 12A and 12B are each an explanatory view of a state of operation using the guidewire according to the sixth embodiment.
Figure 12B:
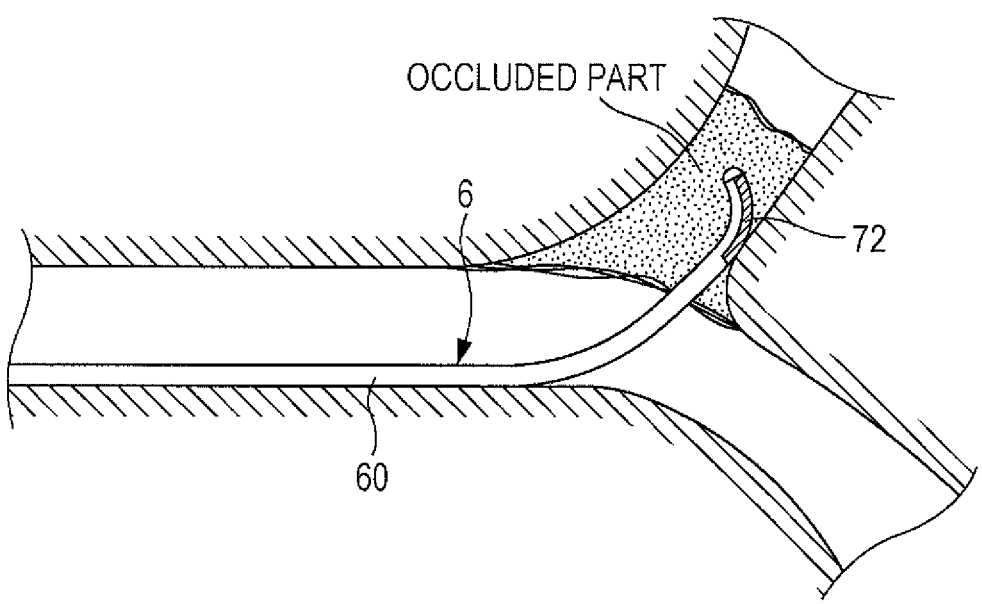

FIGS. 12A and 12B are each an explanatory view of a state of operation using the guidewire 6 according to the sixth embodiment. As described above, as with the guidewire 2 according to the second embodiment, the guidewire 6 according to the sixth embodiment includes the low lubricant portion 72. Therefore, it is possible to achieve the same advantageous effects as those of the guidewire 2 according to the second embodiment. That is, as shown in FIG. 12A, even if the guidewire 6 receives an opposing force from an occluded part, a friction force that acts between the low lubricant portion 72 and an inside wall of a blood vessel (or the structure of the occluded part) allows the guidewire 6 to be reliably inserted into the occluded part.

Since the guidewire 6 according to the sixth embodiment has the above-described structure (see FIGS. 11A and 11B), when the guidewire 6 receives resistance from its distal end side, the guidewire 6 is easily bent in the direction in which the guidewire 6 is curved. Therefore, when the guidewire 6 is further pushed in from the state shown in FIG. 12A, the resistance from the occluded part causes the distal end of the guidewire 6 to be bent in the direction in which the guidewire 6 is curved.

In this way, the distal end of the guidewire 6 can be oriented in the direction of a center axis of a blood vessel from a wall side of the blood vessel at the occluded part. Therefore, when inserting the guidewire 6 into the occluded part, it is possible to suppress rubbing between the low lubricant portion 72 and the inside wall of the blood vessel at the occluded part. As a result, it is possible to more smoothly insert the guidewire 6 into the occluded part.

Figure 13:
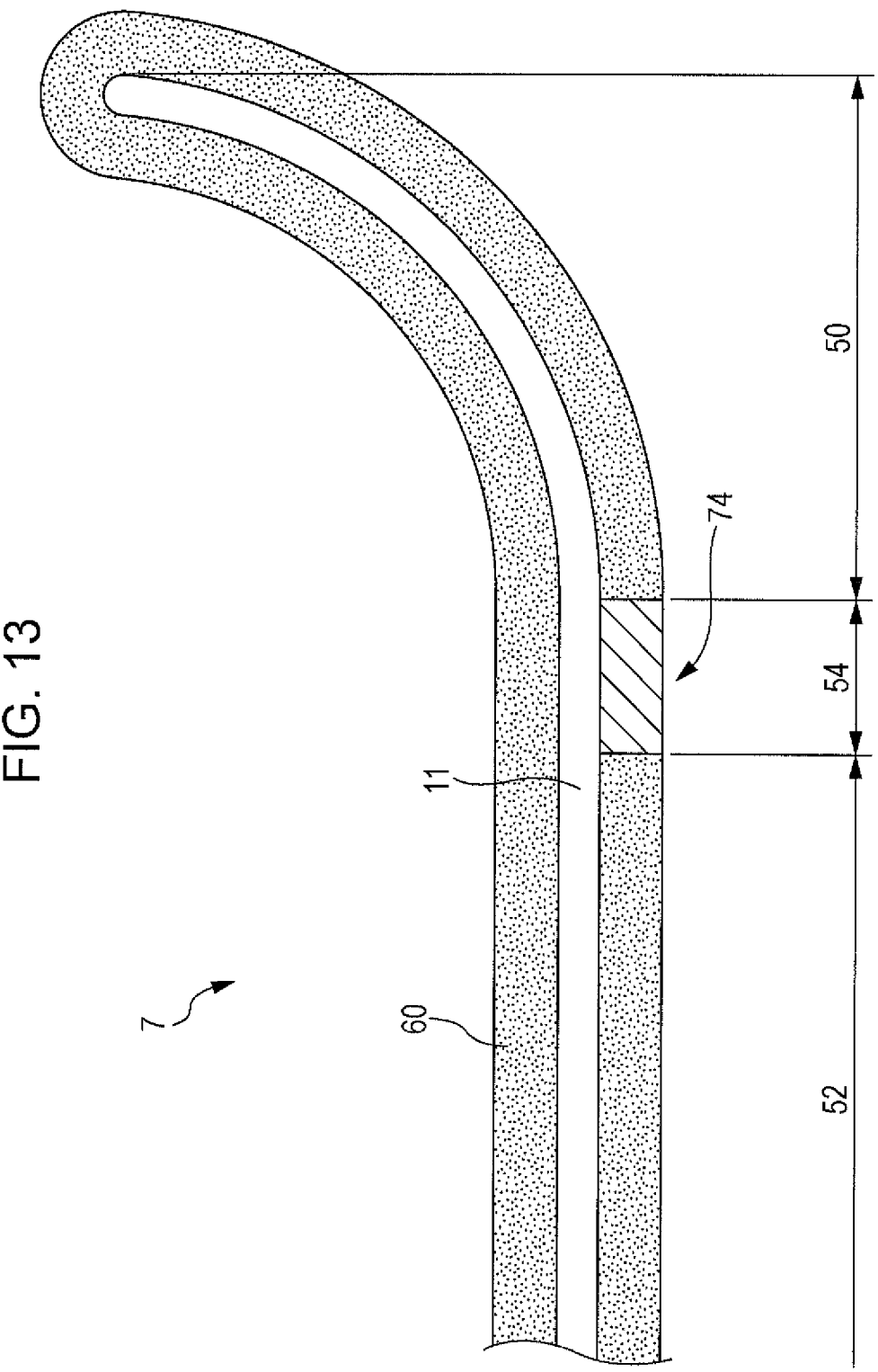
FIG. 13 is an explanatory view exemplifying a case in which the present invention is applied to a guidewire that does not include a coil body at its distal end side.

Although various embodiments have been described, the present invention is not limited to the above-described embodiments, so that modifications may be made. For example, the above-described guidewires according to the embodiments are described as including a coil body 20 at the distal end portion 14 of the core shaft 10. However, the guidewires need not include a coil body 20. Similar advantageous effects may be achieved even if the present invention is applied to a guidewire that does not include a coil body 20. FIG. 13 exemplifies a case in which a surface of a core shaft 11 is provided with a lubricant portion 60 and in which, in a guidewire 7 whose distal end has a curved shape, a low lubricant portion 74 is provided at a boundary portion 54 disposed on a side of the guidewire opposite of a direction toward which a curved portion 50 is curved.

What is claimed is:

1. A guidewire comprising:
   a core shaft; and
   a coil body surrounding the core shaft;
   wherein the guidewire includes;
      a linear portion in which the core shaft and the coil body are linear;
      a curved portion in which the core shaft and the coil body are curved, the curved portion being provided distally of the linear portion;
      a boundary portion that is provided between the linear portion and the curved portion;
      a lubricant portion that is provided on a surface of the linear portion and on a surface of the boundary portion disposed on a side of the guidewire facing a direction toward which the curved portion is curved; and
      a low lubricant portion that is provided at least on a surface of the boundary portion disposed on a side of the guidewire opposite of a direction toward which the curved portion is curved, a lubricating ability of the low lubricant portion being lower than a lubricating ability of the lubricant portion.

2. The guidewire according to claim 1, wherein the low lubricant portion also is provided on a distal end of the curved portion from the boundary portion disposed on the side of the guidewire opposite of the direction toward which the curved portion is curved.

3. The guidewire according to claim 2, wherein the low lubricant portion is provided on the entire surface of the curved portion and the distal end of the curved portion.

4. The guidewire according to claim 1, wherein the low lubricant portion is formed by removing a portion of the lubricant portion that is provided on a surface of the guidewire.

5. The guidewire according to claim 1, wherein:
   the coil body is disposed at the curved portion, the boundary portion, and a distal end of the linear portion, and
   the lubricant portion and the low lubricant portion are provided on an outer surface of the coil body.

6. The guidewire according to claim 5, further comprising:
   an inner coil body surrounding the core shaft disposed inside of the coil body,
   wherein at the curved portion, a curvature of the inner coil body is greater than a curvature of the outer coil body.

7. A guidewire comprising:
a core shaft; and
a coil body surrounding the core shaft,
wherein the guidewire includes:
- a first linear portion in which the core shaft and the coil body are linear;
- a second linear portion in which the core shaft and the coil body are linear, the second linear portion being provided distally of the first linear portion;
- a bent portion that is provided between the first linear portion and the second linear portion;
- a lubricant portion that is provided on a surface of the first linear portion and on a surface of the bent portion disposed on a side of the guidewire facing a direction toward which the bent portion is bent; and
- a low lubricant portion that is provided at least on a surface of the bent portion disposed on a side of the guidewire opposite of a direction toward which the bent portion is bent, a lubricating ability of the low lubricant portion being lower than a lubricating ability of the lubricant portion.

8. The guidewire according to claim 7, wherein the low lubricant portion also is provided on a distal end of the second linear portion from the bent portion disposed on the side of the guidewire opposite of the direction toward which the bent portion is bent.

9. The guidewire according to claim 8, wherein the low lubricant portion is provided on the entire surface of the second linear portion.

10. The guidewire according to claim 7, wherein the low lubricant portion is formed by removing a portion of the lubricant portion that is provided on a surface of the guidewire.

* * * * *